(12) United States Patent
Zhang

(10) Patent No.: US 12,385,059 B2
(45) Date of Patent: Aug. 12, 2025

(54) METHOD AND FORMULATION FOR INDUCING ABORTION OR DEFORMATION OF PLANT SEEDS

(71) Applicant: Zhengzhou Fruit Research Institute, CAAS, Henan (CN)

(72) Inventor: Ying Zhang, Henan (CN)

(73) Assignee: Zhengzhou Fruit Research Institute, CAAS, Zhengzhou (CN)

( * ) Notice: Subject to any disclaimer, the term of this patent is extended or adjusted under 35 U.S.C. 154(b) by 712 days.

(21) Appl. No.: 17/478,913

(22) Filed: Sep. 18, 2021

(65) Prior Publication Data
US 2021/0403940 A1    Dec. 30, 2021

Related U.S. Application Data

(63) Continuation-in-part of application No. PCT/CN2020/083508, filed on Apr. 7, 2020.

(30) Foreign Application Priority Data

Nov. 14, 2019   (CN) .......................... 201911112027.9

(51) Int. Cl.
  *C12N 15/82*   (2006.01)
  *C07K 14/41*   (2006.01)
  *C07K 14/415*  (2006.01)

(52) U.S. Cl.
  CPC ........ *C12N 15/8287* (2013.01); *C07K 14/415* (2013.01)

(58) Field of Classification Search
  None
  See application file for complete search history.

(56) References Cited

U.S. PATENT DOCUMENTS 9,878,004 B2 *  1/2018  Williams ............ A61K 38/1767
2013/0340120 A1 * 12/2013 Louwers ............ C12N 15/8261
                                                    800/290

OTHER PUBLICATIONS

Xiaoqing Xie et al., VqDUF642, a gene isolated from the Chinese grape Vitis quinquangularis, is involved in berry development and pathogen resistance, Planta, Jul. 16, 2016, pp. 1075-1094, vol. 244.

Esther Zúñiga-Sánchez et al., BIIDXI, the At4g32460 DUF642 gene, is involved in pectin methyl esterase regulation during *Arabidopsis thaliana* seed germination and plant development, BMC Plant Biology, Dec. 2, 2014, pp. 1-13, vol. 14, No. 338.

José E. Cruz-Valderrama et al., Degree of pectin methyl esterification in endosperm cell walls is involved in embryo bending in *Arabidopsis thaliana*, Biochemical and Biophysical Research Communications, Nov. 12, 2017, pp. 639-645, vol. 495.

Christoph Maas et al., Mechanism and optimized conditions for PEG mediated DNA transfection into plant protoplasts, Plant Cell Reports, 1989, pp. 148-151, vol. 8.

International Search Report of PCT Patent Application No. PCT/CN2020/083508 issued on Aug. 12, 2020.

* cited by examiner

*Primary Examiner* — Brent T Page

(57) ABSTRACT

The present disclosure relates to the field of genetic breeding, in particular, to methods and formulations for inducing abortion or deformation of plant seeds by a VvDUF642 gene. The result of the present disclosure shows that the VvDUF642 gene is continuously expressed at a high level in seedless varieties, but there is no significant change in expression in nucleated varieties. After the VvDUF642 gene is transformed into an *Arabidopsis*, *Arabidopsis* seeds are deformed. After the VvDUF642 gene is transformed into a tomato, it causes abortion of tomato seeds. The gene or protein can be used for the construction or screening of seed abortion grape varieties.

3 Claims, 7 Drawing Sheets

Specification includes a Sequence Listing.

I : Red Globe  
II : Centennial Seedless  
III : Sunshine Rose  
IV : Red Face and Seedless  
V : Seedless and White  
VI : Early Sweet Rose  
VII : Rose Fragrance  
VIII : Drunk Gold Fragrant and Nucleated  
IX : Drunk Gold Fragrant and Seedless  
X : Sunshine Rose and Nucleated  
XI : Sunshine Rose and Seedless

Wild-type control

*VvDUF642* gene transgenic Arabidopsis

METHOD AND FORMULATION FOR INDUCING ABORTION OR DEFORMATION OF PLANT SEEDS

CROSS-REFERENCE TO RELATED APPLICATIONS

The present application is a Continuation-In-Part Application of PCT application No. PCT/CN2020/083508 filed on Apr. 7, 2020, which claims the benefit of Chinese Patent Application No. 201911112027.9 filed on Nov. 14, 2019. The contents of the above-identified applications are hereby incorporated by reference.

TECHNICAL FIELD

The present disclosure relates to the field of genetic breeding, in particular, to methods and formulations for inducing abortion or deformation of plant seeds, further, to methods for inducing abortion or deformation of plant seeds by a VvDUF642 gene.

SUBMISSION OF SEQUENCE LISTING ON ASCII TEXT FILE

The Sequence Listing is submitted as an ASCII formatted text file via EFS-Web, with a file name of "Sequence_listing.txt", a creation date of Sep. 17, 2021, and a size of 5,458 bytes. The Sequence Listing filed via EFS-Web is part of the specification and is incorporated in its entirety by reference herein.

BACKGROUND

Grapes (*Vitis* spp.) belong to *Vitis* berries of Vitaceae, and their fruits can be widely used in wine making, fresh-eating, juice making, and drying. Grape fruits are loved by people because of their palatable sweet and sour, rich flavor, and rich nutrition. Among them, natural seedless grapes are very popular because it is easy to cultivate, process, and eat them. In developed countries, more than 50% of fresh-eating and dried grapes consumed are seedless varieties. Natural seedless formation pathways of grapes are divided into Parthenocarpy and Stenospermacarpy (seed abortion). Among them, Parthenocarpy is caused by poor pollination and fertilization, which mainly produces seedless fruit seeds that are occasionally seen in the ears of nucleated varieties. While the seed abortion means that after normal fertilization of a grape, the seed abortion occurs to form a natural seedless fruit. The seed abortion is the most stable way for a grape to form a seedless fruit, and it is also an important genetic characteristic that needs to be maintained in the cultivation of a seedless variety. The efficiency of cultivating a new seedless grape variety can be improved by using modern molecular biology methods to study the molecular mechanism and genetic rule of the formation of seedless grapes.

Scientists have carried out extensive research on the genetic mechanism of seedless grapes and made good progress with the help of modern molecular biology research methods. Grape is a close-flowered pollinating plant and has been fertilized at the time of flowering. Therefore, the study of grape seed development often starts from before flowering. Professor Michael Striem maps the abortion process of a grape seed according to the development of a grape seed. It takes fertilization as the core and is divided into ovule stage (before flowering), fertilization stage (flowering), seed coat development stage (5-10 days after flowering), endosperm development stage (11-30 days after flowering), and embryo development stage (31-40 days after flowering). After completing the entire development process, a normal seeded fruit is formed. If the seed is aborted, it will leave a residual nucleus or a seed mark, forming a seedless fruit. The applicant uses slices to continuously observe a seed development process and completely records an abortion process of the seed. The result shows that seeds of a seedless grape variety can be fertilized normally, but abortion occurs because the seed coat fails to develop normally. The seed coat development stage is determined to be a critical period of the abortion. In viticulture and production, some varieties such as "Sunshine Rose" can use gibberellic acid (GA) to obtain seedless fruits by processing ears after flowering. The processing time is 5-7 days after flowering (seed coat development stage), indicating that GA interferes with normal seed coat development and can cause seed abortion.

SUMMARY OF THE DISCLOSURE

In view of this, the technical problem to be solved by the present disclosure is to provide a method for inducing seed abortion by a VvDUF642 gene.

The present disclosure provides a method for inducing abortion or deformation of a plant seed by any of the following I) to V):
  I) a VvDUF642 protein;
  II) a protein that has one or more amino acids substituted, deleted, or added in an amino acid sequence of a VvDUF642 protein and has a same or similar function as the VvDUF642 protein;
  III) a nucleic acid molecule encoding the protein of I) or II);
  IV) a nucleic acid molecule that has substituted, deleted, or added one or more nucleotides in a nucleotide sequence of the nucleic acid molecule of III) and can encode a protein having the same or similar function;
  V) a substance capable of enhancing a level or an activity of at least one of I)-IV).

In the present disclosure, the substance that induces abortion or deformation of the plant seed is the VvDUF642 protein.

The amino acid sequence of the VvDUF642 protein is set forth in SEQ ID NO: 1.

The sequence of the nucleic acid molecule encoding the protein shown in SEQ ID NO: 1 is set forth in SEQ ID NO: 2.

In the present disclosure, the plant that can cause seed deformation or abortion is from Vitaceae, Cruciferae, or Solanaceae. In some embodiments, the plant for experimental verification is a grape, an *Arabidopsis*, or a tomato.

The experiment of the present disclosure shows that the VvDUF642 gene is continuously expressed at a high level in seedless varieties, but there is no significant change in expression in nucleated varieties. After the VvDUF642 gene is transformed into an *Arabidopsis, Arabidopsis* seeds are deformed; after the VvDUF642 gene is transformed into a tomato, it causes abortion of tomato seeds.

The present disclosure also provides a formulation for causing abortion or deformation of a plant seed, comprising at least one of the following i)-v):
  i) a VvDUF642 protein or a nucleic acid molecule encoding the VvDUF642 protein;

ii) an expression vector comprising a nucleic acid encoding a VvDUF642 protein;
iii) a recombinant host comprising ii);
iv) a promoter or an enhancer that enhances expression of a VvDUF642 gene;
v) an inducer that promotes expression of a VvDUF642 gene.

The present disclosure also provides a method for causing abortion of a plant seed, comprising: enhancing a level and/or an activity of an endogenous VvDUF642 protein in a plant, or expressing the VvDUF642 protein in a plant that does not comprise a VvDUF642 gene.

In some specific embodiments, a method of expressing the VvDUF642 protein in the plant that does not comprise the VvDUF642 gene comprises:
constructing an expression vector comprising a nucleic acid encoding the VvDUF642 protein, transforming the expression vector into an *Agrobacterium* strain; and
infecting the plant seed or an explant with the *Agrobacterium* strain.

In the present disclosure, the nucleic acid sequence encoding the VvDUF642 protein is shown in SEQ ID NO: 2.

A backbone vector of the expression vector is pCAMBIA1303, and insertion sites of the nucleic acid sequence encoding the VvDUF642 protein are Nco I and Bst E II.

The recombinant host is *Agrobacterium*, specifically *Agrobacterium* LBA4404.

VvDUF642 can also be used as a marker for screening and breeding of a seedless grape.

The detection of the present disclosure includes the detection of expression or an activity level.

In embodiments of the present disclosure, Western blot is used to detect the expression level of the VvDUF642 protein; Real-time PCR is used to detect the transcription level of the VvDUF642 gene.

Meanwhile, the present disclosure provides a method for screening a seedless grape germplasm resource, comprising:
detecting a transcription level of a VvDUF642 gene of grape germplasm, or detecting an expression level or an activity of a VvDUF642 protein.

A sample tested is a young leaf of a grape vine.

Using the screening method of the present disclosure and only detecting young leaves of a grape vine, the prediction of whether the grape fruit has a seed can be achieved, and the breeding cycle can be shortened.

The present disclosure focuses on the critical period of seed abortion, and separates and collects seed embryos of nucleated and seedless varieties 5-7 days after flowering as core test materials. A transcriptome analysis and a protein expression analysis are carried out. 60 proteins specifically expressed are screened and obtained. After further screening by Western hybridization technology, the VvDUF642 protein, which is highly expressed in seedless grapes, is obtained. The transcriptome result shows that the VvDUF642 gene is continuously expressed at a high level in seedless varieties, but there is no significant change in expression in nucleated varieties. After the VvDUF642 gene is transformed into an *Arabidopsis*, *Arabidopsis* seeds are deformed; after the VvDUF642 gene is transformed into a tomato, it causes abortion of tomato seeds. The gene or protein can be used for the construction or screening of seed abortion grape varieties.

EMBODIMENTS

The present disclosure provides a method for inducing abortion or deformation of a plant seed by a VvDUF642 gene. Those skilled in the art can learn from the content of this disclosure and appropriately improve process parameters to achieve. In particular, it should be pointed out that all similar replacements and modifications are obvious to those skilled in the art, and they are all deemed to be included in the present disclosure. The method and application of the present disclosure have been described through preferred embodiments. Relevant persons can obviously make changes or appropriate changes and combinations to methods and applications herein without departing from the content, spirit and scope of the present disclosure to achieve and apply the technology of the present disclosure.

Reagents and consumables used in the present disclosure are all common commercial products, which can be purchased in the market.

The nucleic acid molecule encoding a VvDUF642 protein includes genomic DNA, cDNA, recombinant DNA or mRNA, hnRNA encoding the VvDUF642 protein, or nucleic acid molecules that are reverse complementary to the above-mentioned DNA, cDNA, recombinant DNA or mRNA. In the present disclosure, "VvDUF642" is the same as "DUF642" and "DUF".

The above-mentioned nucleic acid molecules can be modified or optimized according to actual needs to make gene expression more efficient. For instance, (1) according to preferred codons of a recipient plant, codons of the VvDUF642 gene are changed to conform to preference of the recipient plant while maintaining the amino acid sequence of the VvDUF642 gene of the present disclosure. (2) Or the gene sequence adjacent to the initiating methionine is modified to enable efficient translation initiation. For example, a known effective sequence in plants is used for modification. (3) The above-mentioned nucleic acid molecules are linked to promoters expressed by various plants to facilitate their expression in plants. The promoter may include constitutive, inducible, timing adjustment, developmental regulation, chemical regulation, tissue preference, and tissue-specific promoters. The choice of a promoter will vary with needs of expression time and space, and also depends on the target species. (4) An enhancer sequence is introduced, such as an intron sequence (e.g. from Adhl and bronzel), and a viral leader sequence (e.g. from TMV, MCMV, and AMV).

In the present disclosure, the vector can be a plasmid, a cosmid, a phage, or a virus vector. The host can be a fungus, a bacterium, algae, or a cell.

For a plant that does not contain the VvDUF642 gene, a chemical method, a shotgun method, microinjection, electroporation and other methods can be used to introduce a VvDUF642 gene fragment into a plant cell.

The present disclosure is further described below with reference to examples:

Example 1

Figure 1:
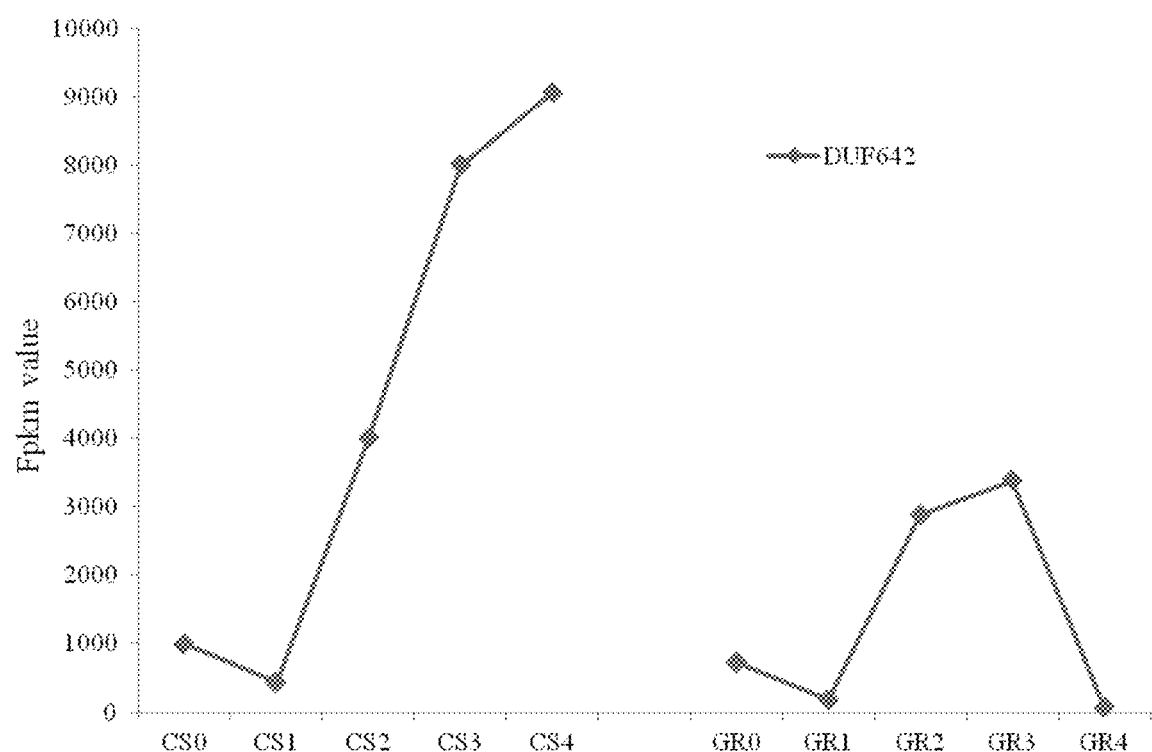
FIG. 1 is a diagram showing the expression of the DUF642 gene transcription level; CS is Centennial Seedless, GR is Red Globe.

1. The expression of the DUF642 gene in seedless varieties is significantly higher than that in nucleated varieties. Transcriptome sequencing was performed on five stages of fruit development [ovule stage (before flowering), fertilization stage (flowering), seed coat development stage (5-10 days after flowering), endosperm development stage (11-30 days after flowering), embryo development stage (31-40 days after flowering)] of a seedless variety (Centennial Seedless) and a nucleated variety (Red Globe). The result showed that the expression of this gene did not differ significantly between the ovule stage and the fertilization stage; from the seed coat development stage, the expression of the DUF642 gene in the seedless variety continuously increased, but the expression in the nucleated variety did not change significantly (FIG. 1).

Figure 2:
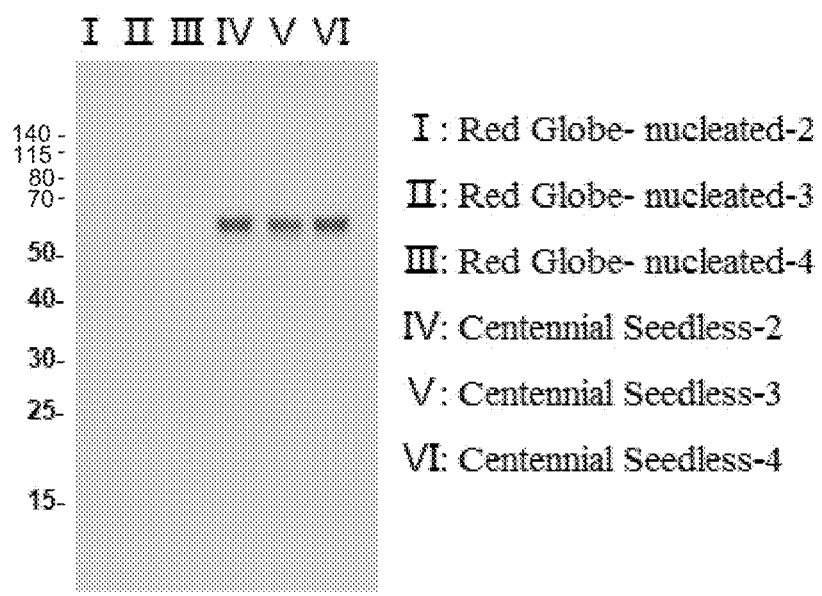
FIG. 2 is a diagram showing the difference of the DUF642 protein expression between Red Globe and Centennial Seedless.
Figure 3:
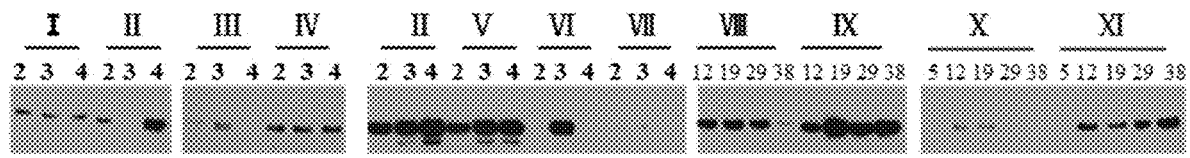
FIG. 3 is a diagram showing the difference in expression of the DUF642 protein between nucleated and non-nucleated varieties.

2. During fruit development, the expression of the DUF642 protein in seedless varieties is significantly higher than that in nucleated varieties (FIG. 2). Detected by western blot, the expression of the DUF642 protein in Seedless and White was much higher than that in Rose Fragrant (FIG. 3).

3. Large sample verification: eight varieties and two de-seeded fruits at the developmental stage were selected as samples for western blot verification. During fruit development, the DUF642 protein was highly expressed in seedless varieties, while low expressed in nucleated varieties. The DUF642 protein expression increased after seedless treatment of Drunk Gold Fragrant and Sunshine Rose. These results confirmed the close linkage between the expression of the DUF642 gene and the seedless trait of grapes (FIG. 3).

4. RNA extraction

Young leaves of a grape vine were selected to extract plant total RNA by a Bioteke plant RNA extraction kit. Thermo Scientific Nanodrop 1000 Micro UV-Vis Spectrophotometer was used to measure the concentration and to confirm the integrity of RNA by agarose gel electrophoresis. A RR047 reverse transcription kit of TaKaRa was used to obtain the first strand of cDNA as a template for PCR cloning.

5. Obtaining of the DUF642 cDNA sequence:

The Primer Find in Vector NTI 11 was used to design primers to clone the DUF642 gene sequence. The primers are shown in Table 1. NEB's Phusion™ ultra-fidelity enzyme was used for PCR amplification. The reaction system was: HF buffer 10 μL, 2.5 mmol/L dNTPs 2.5 μL, template 2 μL, upstream and downstream primers (10 mmol/L) 2.5 μL each, Phusion ultra-fidelity enzyme 0.5 μL, and double distilled water to 50 μL. The PCR reaction program was: pre-denaturation at 98° C. for 3 min; denaturation at 98° C. for 10 s, annealing at 58° C. for 10 s, extending at 72° C. for 30 s, a total of 31 cycles; the final extending at 72° C. for 10 min, and storage at 4° C. The PCR products were electrophoresed on 2% agarose gel, and the amplified products were recycled by an Omega Gel extract recovery kit. TaKaRa EXTaq™ polymerase plus A were used on the products purified, and the reaction system was: 10× buffer 2 μL, 2.5 mmol Mg$^{2+}$ 2 μL, 2.5 mmol/L dNTPs 2 μL, and template 14 μL. Reaction program: 72° C. for 10 min. A DUF642-T vector was constructed according to the pGEMT-easy TM vector construction instruction, and transformed into DH5a *Escherichia coli* (*E. coli*) for blue-white spot screening. A single clone was selected for sequencing by Sangon Biotech (Shanghai) Co., Ltd. Sequencing primers were universal primers of T7 and T7 Terminal.

TABLE 1

| cloning primers of the DUF642 gene | |
|---|---|
| Primer name | Primer sequence 5'-3' |
| DUF642F | atgagagctgtggcgtttcttttgcta (SEQ ID NO: 3) |
| DUF642R | ttagatgtgcctaggaggagtgtgcgga (SEQ ID NO: 4) |

6. The cDNA sequence of the DUF642 gene is shown in SEQ ID NO: 2.

Example 2 DUF642 Gene Causes Seed Deformation in *Arabidopsis*

1. Construction of the plant expression vector: the sequence-verified DUF642-T plasmid was used as a PCR amplification template. pCAMBIA1303 was chosen as a plant expression vector. *Agrobacterium* strain was LBA4404. NEB's NCOI, Bst EII endonucleases, and Axygen small amount plasmid extraction kit were purchased from Zhengzhou Bomei Company. ½ MS, Hygromycin B, Kanamycin, etc. were purchased from Zhengzhou Baosai Biology Company. PEG4000, Cellulase R10, Mecerozym R10, mannitol, potassium chloride, MES, BSA, 0.45 μm filter head, etc. were purchased from Zhengzhou Chaoyan Biology Company. Then the plant expression vector pDUF642 was constructed.

2. With reference to the method of Maas C (Maas et al, 1989), an *Arabidopsis* protoplast was prepared and transformed. A confocal laser microscope was used to observe the *Arabidopsis* protoplast which was transformed and cultured. Nuc Pre was used to analyze and predict a nuclear localization signal.

3. Preparation of competent *Agrobacterium* LBA4404: LB solid medium containing 50 mg/L rifampicin was streaked. A single cell was picked out and shaken in LB liquid medium containing 50 mg/L rifampicin for 48 hours until bacteria solution became turbid. The bacterial solution was inoculated to 50 ml fresh LB liquid medium containing 50 mg/L rifampicin at a ratio of 1:100, and the bacteria were shaken for 5 h. The bacteria solution was placed in an ice bath at 4° C. for 30 min, and centrifuged at 5000 g for 5 min. The supernatant was discarded, and 1 ml of 0.1% calcium chloride was added to suspend; ice bath was performed at 4° C. for 5 min. Then, the solution obtained was centrifuged at 5000 g for 5 min. The supernatant obtained was discarded, and then 800 μL of 0.02% calcium chloride was added for resuspension. The solution obtained was divided into 8 tubes, and 100 μL of solution per tube was placed in an ice bath for later use.

4. 2 μg of plasmid to be transformed was added to the competent *Agrobacterium* prepared. They were mixed, and subjected to liquid nitrogen quick freezing for 1 min, and placed in a water bath at 37° C. for 5 min. 1 ml of LB liquid medium was added into the solution obtained, and then the mixed solution was shaken at 28° C., 200 rpm for 5 h. The solution shaken was concentrated by centrifugation and spread on an LB plate containing 50 mg/L rifampicin and 50 mg/L kanamycin, and cultured at 28° C. for 48 h. Then a single colony was picked for verification.

5. Planting conditions of *Arabidopsis* were as follows: 22° C., 16 h light, 8 h dark, and water enough water two days before transformation. The *Agrobacterium* transformed was shaken to an OD value of about 2.0, and then concentrated and centrifuged at 5000 g for 5 min at room temperature. The supernatant was discarded, and 10% sucrose solution was added for resuspension. The solution obtained was centrifuged at 5000 g for 5 min at room temperature, and the precipitate obtained was resuspended to an OD value of 1.0 by adding 10% sucrose solution. Sillwet L-77 was added to a final concentration of 0.02%. An *Arabidopsis* flower was selected for transformation when a white spot just appeared on the flower. The inflorescence was soaked in an *Agrobacterium* liquid for 1 min, and the filter paper was taken out to absorb the excess liquid on the stem. It was placed in a dark condition at 22° C. for two days, and moisturizing was paid attention to, and then transformation was performed again 7 days later. About three weeks after transformation, the seeds were harvested when the fruit clips were mature.

6. The dried seeds were placed in a 2 ml EP tube, and 900 μL of 70% ethanol containing 0.2% Tween 20 was added into the EP tube. Then the EP tube was shaken for 9 min. The supernatant was discarded, and 90% ethanol was added to wash 3 times. Finally, it was suspended in 100% ethanol and poured on sterilized filter paper to dry. A ½ MS medium was prepared, and hygromycin B was added to a final concentration of 25 mg/L before pouring on the plate. Sterilized *Arabidopsis* seeds were evenly sprinkled on the ½ MS medium, and then sealed and placed in a refrigerator at 4° C. for two days. Then the seeds were transferred into an incubator at 22° C. for cultivation. One week later, the screening result was observed, and the plant that could grow normally was a transgenic *Arabidopsis* positive plant. After continuous screening for two generations, pure T2 generation seeds were obtained for morphological observation.

Figure 4A:
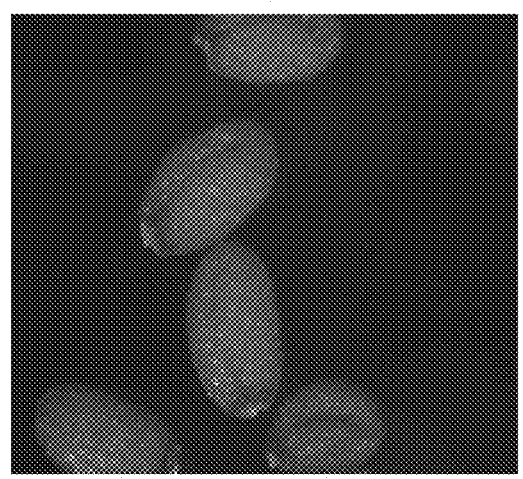
FIG. 4A is a diagram showing the size of *Arabidopsis* seeds.
Figure 4B:
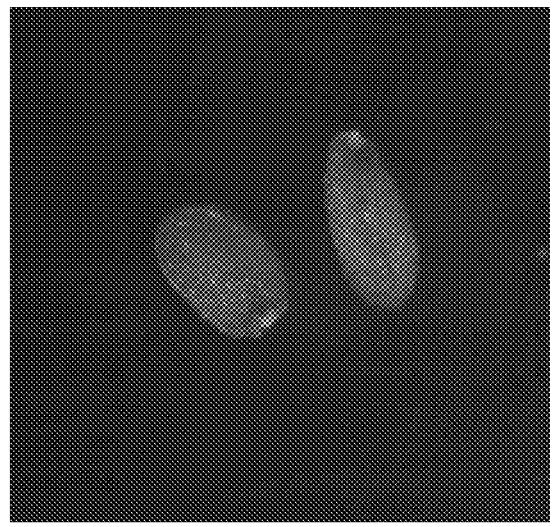
FIG. 4B shows that transgenosis of the DUF642 gene into *Arabidopsis* causes the shapes of *Arabidopsis* seeds to become smaller.

7. Phenotypic Observation:

As shown in FIGS. 4A and 4B, compared with wild-type *Arabidopsis* seeds, transgenosis of the VvDUF642 gene into *Arabidopsis* causes *Arabidopsis* seeds to become smaller.

Figure 5:
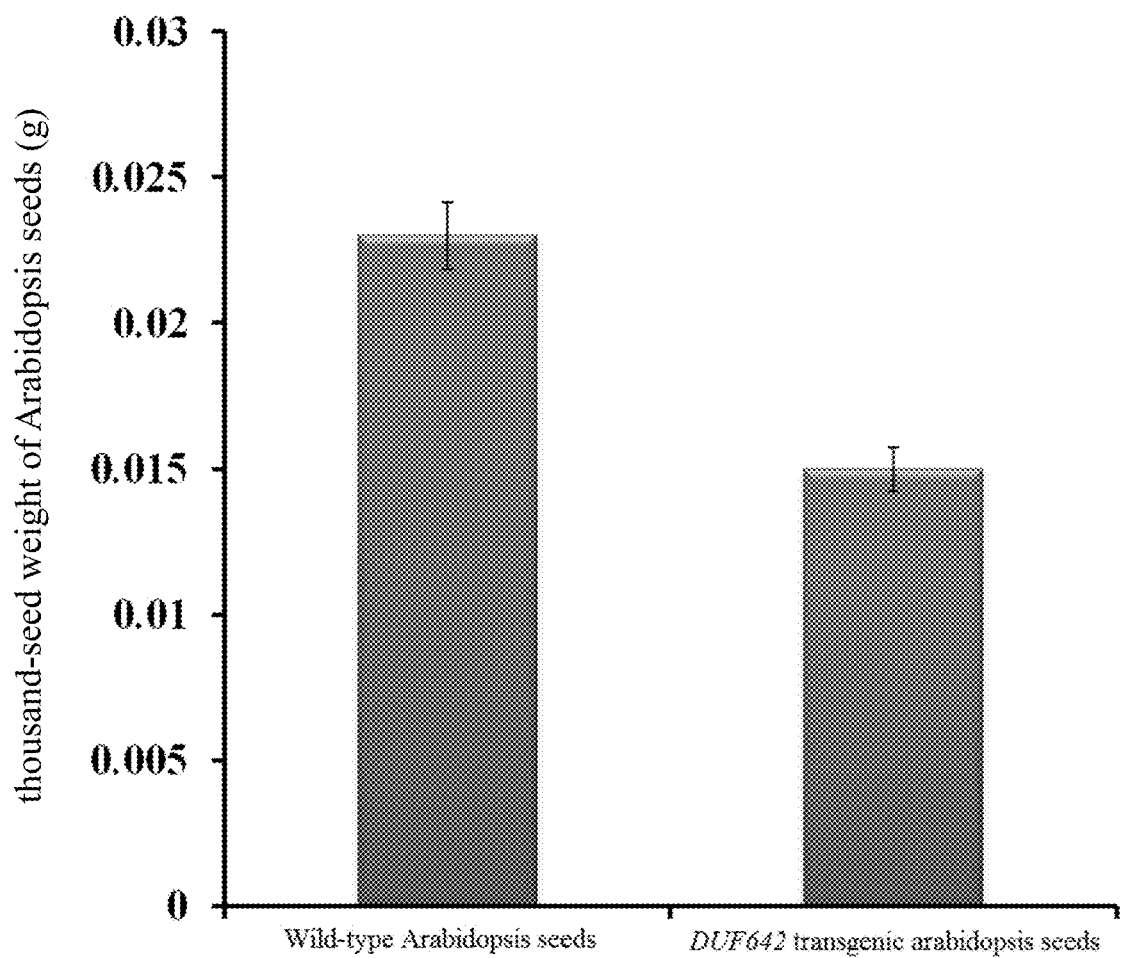
FIG. 5 is a diagram showing that transgenosis of the DUF642 gene into *Arabidopsis* causes a reduction in thousand-seed weight of *Arabidopsis* seeds.

8. Data measurement:

The thousand-seed weight of wild-type *Arabidopsis* seeds and the thousand-seed weight of *Arabidopsis* seeds into which the VvDUF642 gene was transferred was measured and counted. The result is shown in FIG. 5. The result shows that transgenosis of the DUF642 gene into *Arabidopsis* causes *Arabidopsis* seeds to become smaller. The statistical result of thousand-seed weight shows that high expression of the DUF gene causes *Arabidopsis* seeds to become smaller, from 0.023 g of wild type to 0.015 g.

Figure 6:
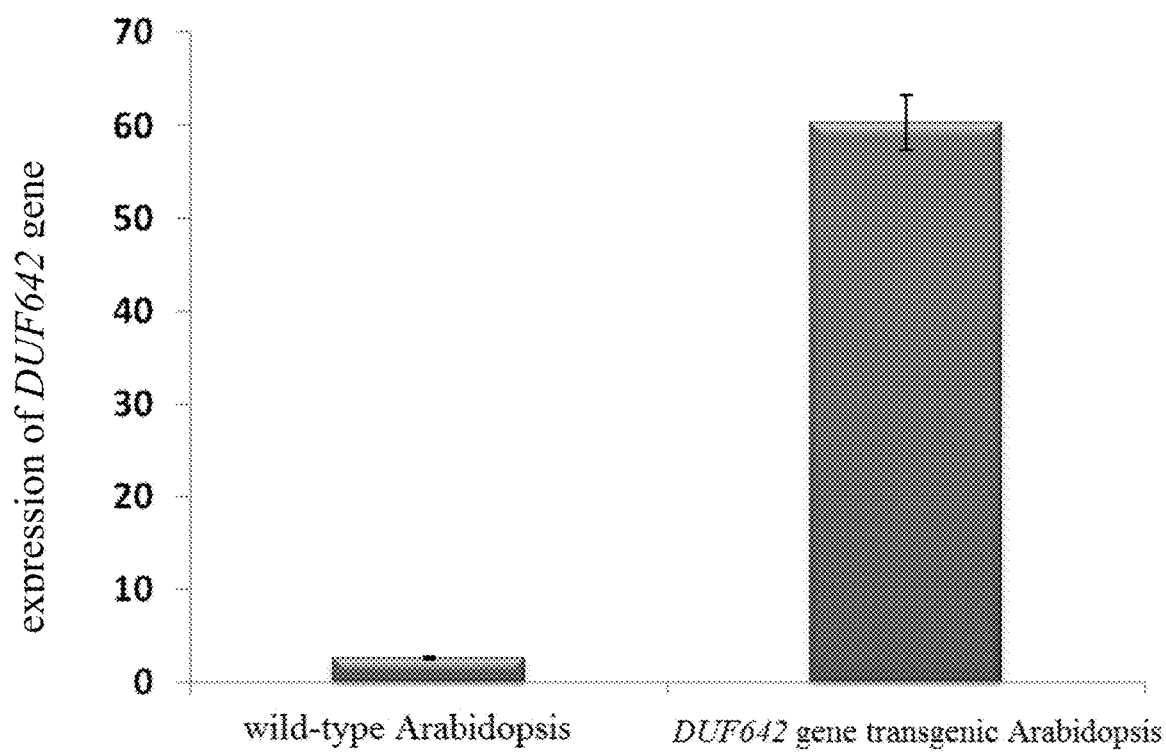
FIG. 6 is a diagram showing expression of the DUF642 gene in wild-type *Arabidopsis* and DUF642 transgenic *Arabidopsis*.

9. DUF642 gene expression data of transgenic *Arabidopsis*:

The expression of the DUF642 gene in wild-type *Arabidopsis* seeds and *Arabidopsis* seeds into which the VvDUF642 gene was transferred was detected and counted. The result is shown in FIG. 6. The result shows that the VvDUF642 gene is highly expressed in transgenic *Arabidopsis*.

Example 3 DUF642 Gene Causes Seed Abortion in Tomatoes

1. Tomato transgenic: the plant expression vector pDUF642 was constructed for tomato transgenic.

Seed sterilization: a few grams of tomato seeds were placed in a sterile Erlenmeyer flask, and first washed with sterile water for 2 minutes, and then washed with 75% alcohol for 1 minute. The seeds were soaked in 5% hypochlorous acid solution for 5-8 minutes, and washed with sterile water for 20 minutes twice, and then placed in a sterile filter board to dry.

2. sowing: sterilized seeds were sown in a culture bottle with a plant spacing of 0.8-1.0 cm. The remaining sterilized seeds were sealed and placed in a dry place for next use. Frequent ultraviolet light irradiation in the ultra-clean table will reduce the germination rate of seeds. The culture bottle sown was placed in the dark for 2 to 3 days. After the seeds appeared white spots and germinated, they were placed in a lighted tissue culture box to grow for 4 to 5 days. Culture conditions: 23±2° C., 16 h/d light, and 8 h/d dark.

3. Preparation of the explants: after tomato seeds grew for 7-8 days, cotyledons were fully expanded. A cotyledon was fetched with a scalpel, and the cotyledon petiole and the cotyledon tip were cut off, leaving the middle part to be cut into 2 to 3 segments as explants.

4. Preculture of the explants: tomato explants were pre-cultured for 1-2 d to expand edges of the explants, which was good for infecting and transforming tomatoes.

5. *Agrobacterium* infection solution: *Agrobacterium* OD600 was 0.1-0.2, and infection time was 10-15 min; pH of MS suspension solution was 5.4. The explants were dried in a sterile filter paperboard, and the filter paperboard can be replaced multiple times to absorb excess *Agrobacterium*.

6. Co-culture: the dried explants were placed in a co-cultivation medium and cultured in the dark for 2 days. Temperature: 23±2° C. The co-cultivation medium was the same as the pre-cultivation medium.

7. Delayed screening: after co-cultivation, the explants were washed twice with 1 g/L cephalosporin aqueous solution for 15 minutes (or washed once with 1 g/L cephalosporin aqueous solution, and washed once with sterile water, each for 15 min). After the explants were dried in the filter paperboard, they were placed in a delayed screening medium, and cultivated under light for 3 to 5 days.

8. Induction and screening of calluses: 30-40 days. Callus differentiation and bud elongation (late seedling differentiation medium): 30-40 days. Rooting: the seedlings to be differentiated grew to about 2-3 cm, and they were excised from the calluses and transferred to a rooting medium; time: 10-15 days.

Figure 7:
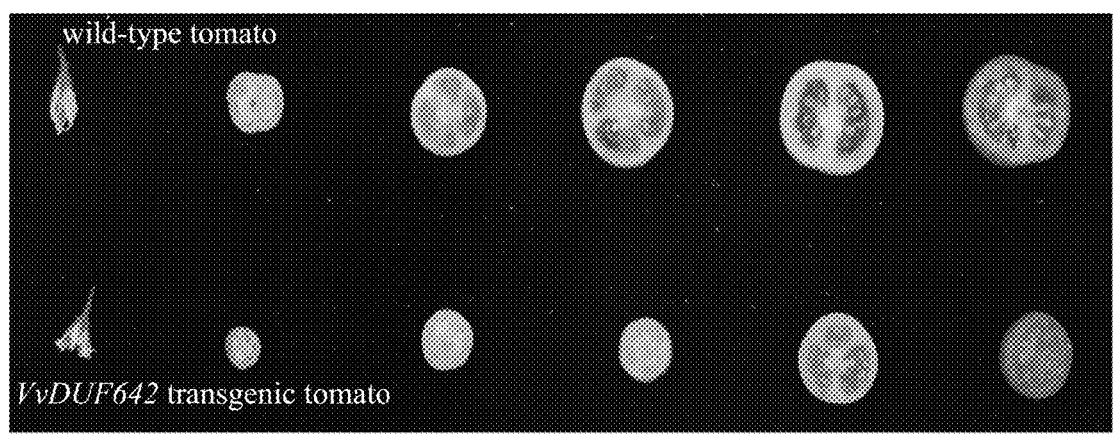
FIG. 7 is a diagram showing that the DUF642 gene causes tomato seeds abortion in tomatoes, forming a seedless fruit and reducing fruit volume.
Figure 8:
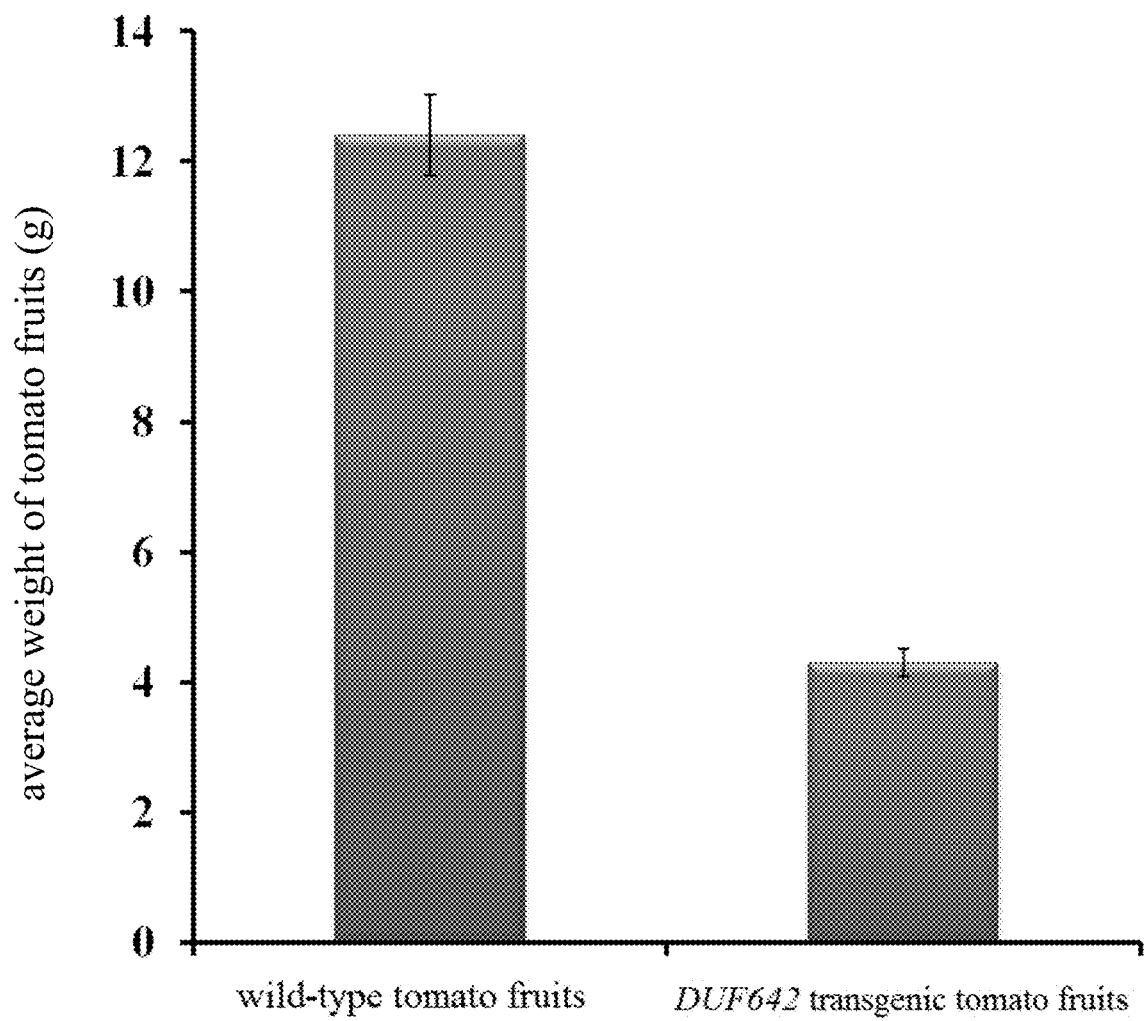
FIG. 8 is a diagram showing that transgenosis of the DUF642 gene into tomato causes a decrease in average fruit weight of tomatoes.

9. Phenotypic observation:

The phenotypes of wild-type tomatoes and tomatoes into which the VvDUF642 gene was transferred were observed. The results showed that transgenosis of the VvDUF642 gene into tomatoes caused abortion of tomato seeds and formation of seedless fruits (FIG. 7). 10. Data measurement:

The average fruit weight of wild-type tomato fruits and tomato seeds into which the VvDUF642 gene was transferred was measured and counted. The result is shown in FIG. 8. The result shows that transgenosis of the DUF642 gene into tomatoes causes tomato fruits to become smaller.

Figure 9:
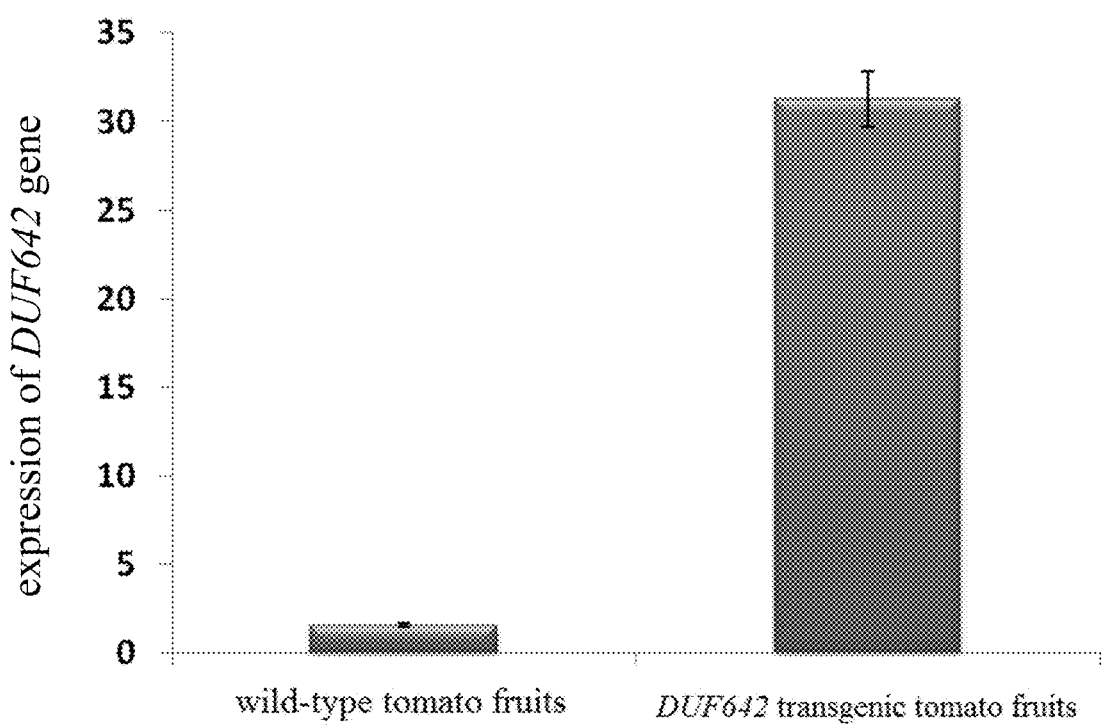
FIG. 9 is a diagram showing expression of the DUF642 gene in wild-type tomatoes and DUF642 transgenic tomatoes.

11. DUF642 gene expression data of transgenic tomatoes:

The expression of the DUF642 gene in wild-type tomato seeds and tomato seeds into which the VvDUF642 gene was transferred was detected and counted. The result is shown in FIG. 9. The result shows that the VvDUF642 gene was highly expressed in transgenic tomatoes.

The examples described above are just preferred examples of the present disclosure, it should be noted that improvements and modifications within the scope of the principle of the disclosure should be regarded as within the scope of protection of the present disclosure to those skilled in the art.

---

What is claimed is:

1. A method for inducing abortion or deformation of a plant seed, comprising inducing the plant seed by a VvDUF642 protein or a nucleic acid molecule encoding the VvDUF642 protein,
wherein the VvDUF642 protein is increased in activity in the plant seed,
wherein the nucleic acid molecule encoding the VvDUF642 protein is overexpressed in the plant seed,
wherein the amino acid sequence of the VvDUF642 protein is set forth in SEQ ID NO: 1,
wherein a sequence of the nucleic acid molecule encoding the VvDUF642 protein is set forth in SEQ ID NO: 2, and
wherein the plant seed is a grape seed, an *Arabidopsis* seed, or a tomato seed.

2. A method for causing abortion of a plant seed, comprising: enhancing a level and/or an activity of an endogenous VvDUF642 protein of claim 1 in a plant, or expressing the VvDUF642 protein in a plant that does not comprise a VvDUF642 gene,
wherein the VvDUF642 protein is increased in activity in the plant seed, and
wherein the plant seed is a grape seed, an *Arabidopsis* seed, or a tomato seed.

3. The method of claim 2, wherein a method of expressing the VvDUF642 protein in the plant that does not comprise the VvDUF642 gene comprises:
constructing an expression vector comprising a nucleic acid encoding the VvDUF642 protein, transforming the expression vector into an *Agrobacterium* strain; and
infecting the plant seed or an explant with the *Agrobacterium* strain.

* * * * *

SEQUENCE LISTING

```
<160> NUMBER OF SEQ ID NOS: 4

<210> SEQ ID NO 1
<211> LENGTH: 368
<212> TYPE: PRT
<213> ORGANISM: Vitis spp.

<400> SEQUENCE: 1

Met Arg Ala Val Ala Phe Leu Leu Leu Leu Cys Ala Thr Cys His
1               5                   10                  15

Ile Ala Leu Ser Phe Thr Asp Gly Leu Leu Pro Asn Gly Asn Phe Glu
            20                  25                  30

Leu Gly Pro Lys Pro Ser Asp Met Lys Gly Thr Glu Val Ile Gly Pro
            35                  40                  45

His Ala Ile Pro Glu Trp Glu Thr Ser Gly Phe Ile Glu Tyr Ile Lys
50                  55                  60

Ala Gly Gln Lys Gln Gly Asp Met Leu Leu Val Val Pro Glu Gly Ala
65                  70                  75                  80

Phe Ala Val Arg Leu Gly Asn Glu Ala Ser Ile Lys Gln Arg Val Lys
                85                  90                  95

Val Ile Lys Gly Met Tyr Tyr Ser Ile Thr Phe Ser Ala Ala Arg Thr
            100                 105                 110

Cys Ala Gln Glu Glu Arg Leu Asn Ile Ser Val Ala Pro Asp Trp Gly
            115                 120                 125

Val Leu Pro Met Gln Thr Leu Tyr Ser Ser Asn Gly Trp Asp Ser Tyr
130                 135                 140

Ala Trp Ala Phe Gln Ala Asp Tyr Asp Val Ile Glu Ile Val Ile His
145                 150                 155                 160

Asn Pro Gly Val Glu Glu Asp Pro Ala Cys Gly Pro Leu Ile Asp Ser
                165                 170                 175

Val Ala Phe Arg Ala Leu Tyr Pro Pro Arg Pro Ser Ser Lys Asn Leu
            180                 185                 190

Leu Lys Asn Gly Gly Phe Glu Glu Gly Pro Tyr Val Phe Pro Asn Thr
            195                 200                 205

Ser Trp Gly Val Leu Ile Pro Pro Asn Ile Glu Asp Asp His Ser Pro
210                 215                 220

Leu Pro Gly Trp Met Val Glu Ser Leu Lys Ala Val Lys Tyr Ile Asp
225                 230                 235                 240

Ser Asp His Phe Ser Val Pro Gln Glu Lys Arg Ala Val Glu Leu Val
                245                 250                 255

Ala Gly Lys Glu Ser Ala Ile Ala Gln Val Ala Arg Thr Ile Pro Gly
            260                 265                 270

Lys Thr Tyr Ala Leu Ser Phe Ser Val Gly Asp Ala Ser Asn Ser Cys
            275                 280                 285

Glu Gly Ser Met Val Val Glu Ala Phe Ala Gly Arg Asp Thr Ile Lys
290                 295                 300

Val Pro Tyr Glu Ser Lys Gly Lys Gly Phe Lys Arg Ala Val Leu
305                 310                 315                 320

Arg Phe Val Ala Val Ser Asn Arg Thr Arg Ile Met Phe Leu Ser Thr
                325                 330                 335
```

```
Phe Tyr Thr Met Arg Ser Asp Asp Tyr Ala Ser Leu Cys Gly Pro Val
            340                 345                 350

Leu Asp Asp Val Lys Leu Leu Ser Leu Arg Thr Pro Pro Arg His Ile
        355                 360                 365

<210> SEQ ID NO 2
<211> LENGTH: 1107
<212> TYPE: DNA
<213> ORGANISM: Vitis spp.

<400> SEQUENCE: 2
atgagagctg tggcgtttct tttgctacta ttgtgcgcca cctgccacat tgccttatcc      60
ttcaccgacg gactattacc gaatgggaac ttcgagctgg ggccgaagcc atcggacatg     120
aagggaacgg aggtgatagg cccgcacgcc ataccggaat gggaaacatc gggtttcatc     180
gagtacataa aagcaggaca aaacaaggc gacatgttgc tggtcgtccc tgaaggagcc     240
ttcgcagtca ggctggggaa cgaggcttcc ataaaacaga gagtgaaggt gatcaaggga     300
atgtactatt ccattacctt tagtgccgcc agaacctgcg cccaggagga gcgcttgaac     360
atatcagtgg cgcccgactg gggagtcctg cctatgcaaa ctctgtacag cagcaacggc     420
tgggactcct acgcctgggc gttccaggct gattacgatg tgatcgagat cgtcatacat     480
aacccaggcg tagaggagga tccagcttgt ggaccgttga tcgattccgt tgctttcagg     540
gctctgtatc ctcccagacc ttccagcaag aacctactga aaatggtgg gtttgaagag     600 ggcccatatg tgttccccaa cacatcctgg ggagttctca tcccacccaa cattgaagat     660
gatcactctc cgctccctgg ttggatggtg gagtccctca agccgtcaa gtacatcgac     720 tccgaccact tctccgtgcc gcaggagaaa cgtgcggtgg agctggtggc cggaaaagag     780
agtgccatag cccaagtagc cagaaccatc cctggcaaaa catatgcgct ctcattctca     840
gtaggagatg ccagcaactc ctgtgaaggg tccatggtgg tggaggcctt cgccggcagg     900
gacaccatca aggtgccata tgaatcaaag ggcaaaggag gcttcaagcg ggctgttctc     960
cgttttgtag cggtatccaa ccgaacccga atcatgttcc tgagcacatt ctataccatg    1020
aggagtgatg actatgcctc cctctgtgga cctgttcttg acgatgtgaa gctgctcagc    1080
ctccgcactc ctcctaggca catctaa                                        1107

<210> SEQ ID NO 3
<211> LENGTH: 27
<212> TYPE: DNA
<213> ORGANISM: Artificial Sequence
<220> FEATURE:
<223> OTHER INFORMATION: Synthetic

<400> SEQUENCE: 3
atgagagctg tggcgtttct tttgcta                                          27

<210> SEQ ID NO 4
<211> LENGTH: 28
<212> TYPE: DNA
<213> ORGANISM: Artificial Sequence
<220> FEATURE:
<223> OTHER INFORMATION: Synthetic

<400> SEQUENCE: 4
ttagatgtgc ctaggaggag tgtgcgga                                         28
```